United States Patent [19]

Robinson et al.

[11] Patent Number: 4,702,256
[45] Date of Patent: Oct. 27, 1987

[54] ELECTRICAL CONNECTOR FOR A DISPOSABLE ELECTRODE

[75] Inventors: Earl F. Robinson, El Toro; Rex O. Bare, Irvine, both of Calif.

[73] Assignee: Andover Medical Incorporated, Haverhill, Mass.

[21] Appl. No.: 938,302

[22] Filed: Dec. 5, 1986

Related U.S. Application Data

[63] Continuation of Ser. No. 664,130, Oct. 24, 1984, abandoned.

[51] Int. Cl.$^4$ ............................................. A61B 5/04
[52] U.S. Cl. .................................. 128/639; 128/798; 403/111; 439/729
[58] Field of Search ............... 128/639, 640, 641, 798, 128/802; 339/17 F, 176 MF, 261; 403/111

[56] References Cited

U.S. PATENT DOCUMENTS 2,793,355  5/1957  Randall et al. ....................... 339/261
3,543,760 12/1970  Bolduc ................................. 128/798

FOREIGN PATENT DOCUMENTS 1345314  1/1974  United Kingdom ................ 339/261

Primary Examiner—William E. Kamm
Assistant Examiner—Randy Citrin
Attorney, Agent, or Firm—Grady J. Frenchick; Reed A. Duthler; John L. Rooney

[57] ABSTRACT

A small plastic connector is provided with a unique electrical contact mounted in one jaw of the connector to mate with an angled edge on the other jaw of the connector to crimp and securely grip a thin, flat, flexible electrode in the connector while making good electrical contact. The jaws and the contact are further constructed so that the conductive surface on the electrode is pressed into engaging with a large contact surface.

6 Claims, 6 Drawing Figures

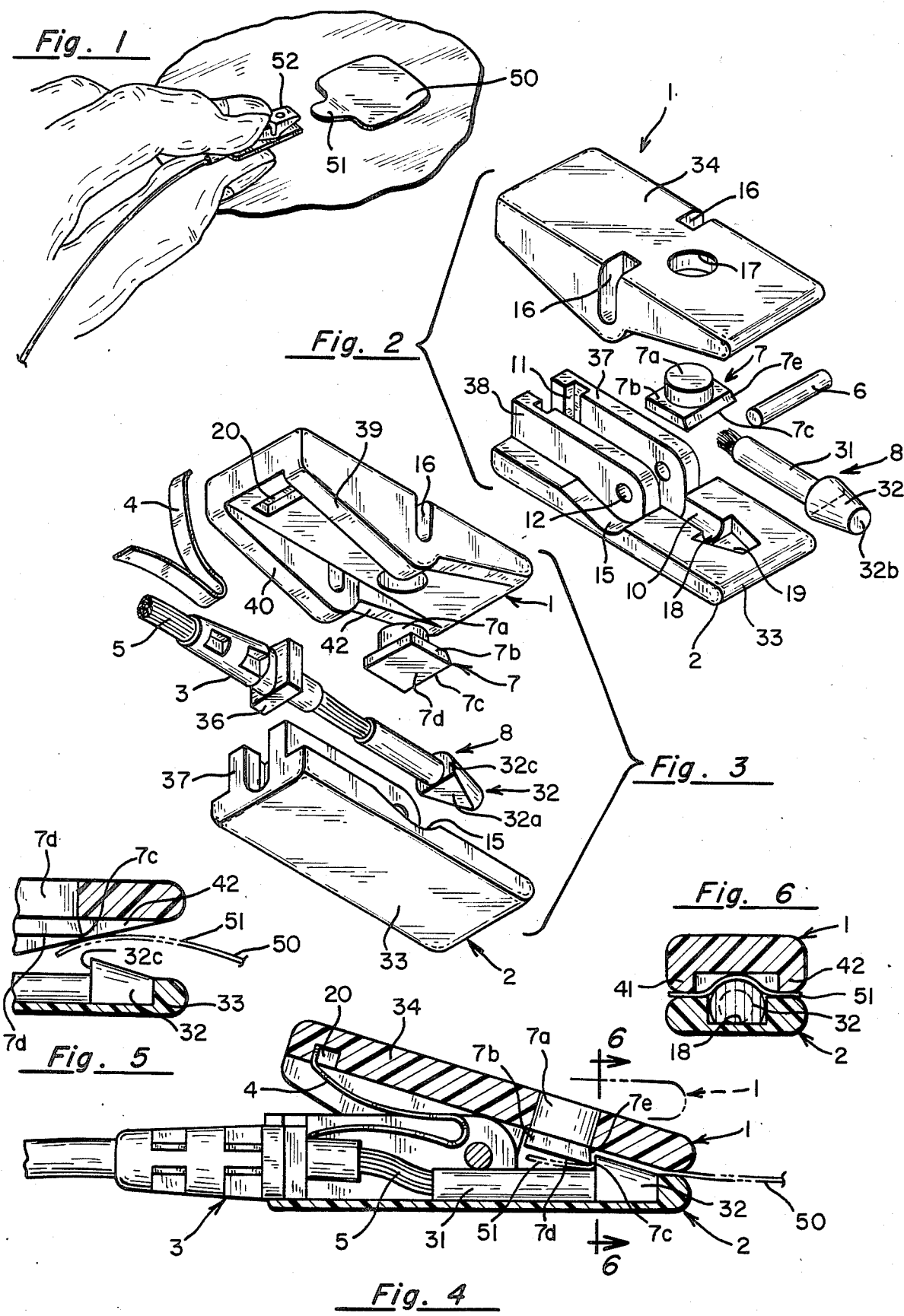

and which extends vertically to perform a strain relief function.
ELECTRICAL CONNECTOR FOR A DISPOSABLE ELECTRODE This is a continuation of co-pending application Ser. No. 664,130 filed on Oct. 24, 1984, now abandoned.

BACKGROUND OF THE INVENTION

I. Field of the Invention

Ths invention pertains to electrical connectors, specifically an electrical connector to grasp a flexible, lightweight electrode.

Doctors in offices, clinics and hospitals around the world use electrocardiograms for diagnostic purposes. To produce electrocardiograms an electrode is applied to the skin and used to detect changes in electrical potential produced by the contractions of the heart. Typically, to make electrical contact with the skin, medical personnel apply a solution and strap large metal electrodes to the body. In some instances, this is done by using a suction cup. Many problems result from this method of applying electrodes. Among the problems are the mess associated with applying a solution to the body, and the storage of the straps, electrodes, suction cups and solutions. Further problems include the inordinate amount of time required by personnel to apply the electrodes and possibility of unsatisfactory electrical contact with the body.

To alleviate these problems a flexible, disposable electrocardiogram electrode was developed. Conductive jell-adhesive applied to a paper-backed conductive foil provides for a lightweight, convenient and disposable electrode. This electrode is easy and quick to apply, and is deformable for application on most any part of the body. Furthermore, it requires no application of an electrolytic solution and is compact and easy to store. The disposable electrode also provides good electrical contact with the skin.

II. Prior Art Relating to Disclosure

Various means exist to connect lead wires to electrodes or electrical terminals. One common type of connector consists of two pivotally mounted, spring biased metal jaws having multiple teeth for gripping an electrical terminal or electrode. One example of this is referred to as an alligator clip.

Problems arise, however, when medical personnel use metal connectors to connect the lead wires from an electrocardiograph to the disposable electrode. The metal connectors are too heavy and tend to pull off the lightweight electrodes. Furthermore, the multi-toothed metal jaws pierce the thin conductive foil. Prior art metal connectors are generally designed to grip much more substantial electrodes. The pointed teeth, associated with the prior art, provide only a small area to disperse the gripping force. Consequently, the metal connectors pierce the thin conductive film with ease. These problems hinder the performance of the disposable electrode by leading to poor electrical contact with the body. As a consequence, some health-care personnel believe disposable electrodes do not work properly.

Because of the problems associated with using a conventional metal connector on the disposable electrode, there is, a definite need for a device that is small, lightweight and which makes electrical contact with the electrode without piercing cam conductive film.

SUMMARY OF THE INVENTION

The electrical connector of the invention is particularly useful in solving many of the problems associated with prior art connectors used with disposable electrodes. The connector is lightweight and will not pull off the disposable electrodes due to a unique gripping surface. This unique surface allows the electrical connector to maintain a good grip on the disposable electrode without piercing the foil conductor. The electrical connector includes a pivotally mounted upper and a lower jaw, preferably made of a lightweight plastic material. Housed within the lower jaw is an electrical contact preferably having a cylindrical portion joined to a generally frustum-shaped portion. The larger end of the frustum adjoins the cylindrical portion and forms an angled shoulder extending toward the upper jaw.

Carried on the upper jaw is an angled edge portion extending toward the lower jaw. The angled edge portion is located so that upon closing it does not engage the shoulder yet extends beyond the shoulder and stops in a position closely adjacent to the shoulder. This allows the angled edge portion and the contact shoulder to crimp the flexible electrode. The jaw is also formed and arranged so that the conductive surface of the electrode is held against the surface of the contact.

DRAWINGS

FIG. 1 is a perspective view of a person using the electrical connector for a disposable electrode.

FIG. 2 is an exploded perspective view of the electrical connector from the top.

FIG. 3 is an exploded perspective view of the electrical connector from the bottom.

FIG. 4 is a cross-sectional view of an assembled electrical connector shown gripping the tab of the disposable electrode.

FIG. 5 is a cross-sectional view of the tip of the electrical connector while in an open position.

FIG. 6 is a cross-sectional view taken along line 6—6 in FIG. 4.

DETAILED DESCRIPTION OF THE PREFERRED EMBODIMENT

Referring to FIGS. 2 and 3, the preferred embodiment of the electrical connector comprises an upper jaw 1 and a lower jaw 2 connected by pivot pin 6, a contact button 7, an electrically conductive contact 8, and a spring 4.

The contact 8 includes an elongated cylindrical body 31 joined at one end to an enlarged tip 32 having in its preferred form a substantially frusto-conical shape. The lower side of this tip is cut to form a flat lower wall 32A which is generally perpendicular to the small and large end surfaces or bases 32b and 32c of the tip. As may be seen, the larger end of the tip is connected to the cylindrical body 31 and has a radius larger than that of the cylindrical body such that the larger end wall 32c of the tip forms a shoulder. The smaller end of the enlarged tip has a radius approximately equal to that of the cylindrical portion 31.

The rear end of the cylindrical body 31 has a cavity shaped to receive the uninsulated portion of an electrocardiograph lead wire 5. Snugly mounted on the insulated portion of the lead wire 5 is a tubular, elongated strain reliever 3 having a centrally located square plate 36 which extends vertically to perform a strain relief function.

The jaws 1 and 2 are preferably made of a strong, lighweight, electrically-insulating plastic material such as phenylene oxide resin, one suitable example being sold under the tradename Ryton, produced by Phillips Petroleum Company. The lower jaw 2 has a generally rectangular shape including a lower base or plate 33 having a generally flat lower surface, as well as a flat upper surface having recesses formed therein and projections extending upwardly therefrom. A pair of parallel walls or projections 38 extend upwardly from the plate 33, and extend from the rear of the plate 33 to a point slightly beyond the lengthwise middle of the plate. The walls also straddle the longitudinal center line of the plate to define a space for receiving the contact body 31, the lead wire 5, and the strain reliever 3. Located toward the rear of the jaw 2 in the inner surface of the walls 37 and 38 are two notches 11 which receive the plate 36 of the strain reliever. Formed on the forward ends of the upstanding walls 37 and 38 are two transversely extending pin holes 12 aligned to receive the pivot pin 6, pivotally connecting the jaws 1 and 2. Also formed in the upper surface of the lower jaw plate 33 are two clearance recesses 15, located outwardly from the walls 37 and 38, generally concentric with the pinholes 12.

Also formed in the upper surface of lower jaw plate 33 is a recess 18, centered along the longitudinal center line of the plate 33. The recess 18 includes a forward trapezoidal portion 19, shaped to receive the lower portion of the contact tip 32 and thus position the contact. The recess also has a semi-cylindrical trough portion 10 for receiving the contact cylindrical portion 31. This trough extends from the base of the trapezoidal portion 19 to the rear of the lower jaw plate 33.

The upper jaw 1 also has a generally rectangular shape including an upper plate with an essentially flat upper surface and a lower parallel surface having internal recesses formed thereon. Two parallel side walls 39 and 40 depend from the outer edges of the plate 34, perpendicular to the plate. These walls depend the greatest amount near the center of the plate and then taper rearwardly. The central lower edges of these walls are curved to generally conform to the recesses 15 in the lower jaw. Located approximately along the shorter center line of the horizontal plate 34 on the outside of the sidewalls 39 and 40, are a pair of pin notches 16 which at their lower ends form openings through the walls 39 and 40, and are aligned with the pinholes 12 of the lower jaw.

Also depending from the upper jaw plate 34 along the outer edges of the plate, are a pair of forwardly extending ramps 41 and 42. As may be seen, the rearward portions of these ramps are adjacent the forward portions of the walls 39 and 40, and the ramps taper upwardly toward the forward tip of the upper jaw.

Also formed in the upper jaw plate 34 is a buttonhole 17 for receiving the upper cylindrical portion 7a of the button 7. Formed in the rear portion of the lower surface of the upper plate 34 is a spring receiving recess or notch 20. The notch is shaped to receive the upper end of the flat, essentially U-shaped spring 4.

Referring to FIG. 4, the connector components are shown in assembled condition with the jaws in closed position. As may be seen, the flat, flexible spring 4 is formed in a loop between the rear of the connector jaws with one end being secured in the notch 20 in the upper jaw and the other end being positioned by the strain reliever plate 36. The contact 8 is shown positioned in its recess 18 in the lower jaw plate 33 with the lead wire 5 and the strain reliever 3 being captured between the vertical walls 37 and 38 on the lower jaw. Note that the upper portion of the frusto-conical tip 32 extends above the upper surface of the lower jaw plate 33 towards the upper jaw 1. However, the forward end of the contact tip 32 is approximately flush with the upper surface of the plate 33.

The contact button cylindrical portion 7a is shown captured in the hole 17 in the upper plate and its lower, generally rectangular portion 7b that extends beyond the cylindrical portion 7a engages the lower surface of the upper jaw plate 34. The forward projecting edge portion 7c formed by a lower surface 7d and forward wall 7e of the button 7b may be seen to be positioned closely adjacent to the shoulder on the contact tip. The forward wall 7e extends at an angle with respect to the lower surface 34a of the upper plate 34 at approximately 75°. The contact shoulder 32c defined by the larger end of the tip, extends at an angle of approximately 90° with the upper and lower surfaces of the lower plate 33. The upper and lower surfaces of the jaw plates in their closed position form an acute angle of approximately 15°. This results in the forward 7e wall of the angled edge 7c being approximately parallel to the contact shoulder 32c when the jaws are in a closed position as shown in FIG. 4.

When the connector 52 of the invention is to be positioned on a flexible electrode 50 of the type shown in FIG. 1, the rear portions of the connector jaws 1 and 2 are gripped and squeezed towards each other to open the jaws. Note that the finger and thumb used for gripping the rear of the jaws are considerably wider than the width of the jaws. This illustrates the miniature nature of the connector. In a preferred form of the invention, the jaws are only about 5/16ths of an inch in width. The electrode has a conductive foil lower surface supported by an upper backing sheet of paper or plastic. The surface of the foil layer to be attached to the patient's body has a suitable conductive adhesive thereon. Such a disposable electrode is marketed by Harco Medical Electronics Devices, Inc. of Irvine, Calif.

Depressing the rear portions of the jaws against the urging of the spring 4, opens the jaw tips as shown in FIG. 5. In this position, the upper jaw plate 34 is approximately parallel to the lower jaw plate 33. This may also be seen in broken lines in FIG. 4. With the jaw tips open, they may be easily placed over the electrode tab 51. since the lower edges of the ramps 41 and 42 extend below the angled edge 7c of the contact button, and since the tab 51 on the flexible electrode is wider than the jaws, the tab is guided between the jaws by the ramps 41 and 42 and cannot catch on the angled edge 7c. Additional guiding action is provided by the upper curved, tapered surface of the contact tip 32 which extends above the upper surface of the lower jaw plate 33. As seen from FIGS. 4 and 5, this surface tapers upwardly and rearwardly, thus also guiding the tab 51 so that the jaws are smoothly placed over the flexible tab.

Releasing the connector jaws causes the spring 4 to move the jaw tips into the closed or gripping position of FIG. 4. Upon closing around the tab 51, the angled relation of the angled edge 7c, the contact tip shoulder 32c, and the jaw tips results in the angled edge 7c just clearing the upper edge of the shoulder 32c of the electrical contact 8, crimping the tab 51 between the angled edge 7c and the contact shoulder 32c. As seen, the shoulder 32c and the angled edge 7c are essentially parallel to each other upon closing, with the distance between them being slightly less than the thickness of the tab 51 so that the tab is securely gripped. Stated otherwise, the angled edge 7c closely overlaps or extends adjacent to the contact shoulder but does not engage it. Thus, it is somewhat in the nature of a shearing action without any cutting or tearing of the somewhat fragile tab. It should also be noted that the angled edge 7c and the contact shoulder 32c extend transversely of the connector, generally perpendicular to the direction that the connector and its lead wire would normally be moved when being placed on or removed from the electrode. That is, the pull of the weight or load of the connector is generally perpendicular to the angled edge and shoulder. This enhances the grip of the connector on the electrode.

In addition, the tab is further gripped between the tips of the upper and lower jaws 1 and 2 and between the contact tip 32 and the upper jaw plate 34.

Another function of the ramps 41 and 42 may be seen from FIG. 6. As the connector jaws close, the flexible electrode tab 51 is engaged by the ramps, pulling the edges of the tab down, thereby wrapping the tab around the curved surface of the enlarged tip portion 32 of the contact 8. The ramps are then closely spaced from the upper surface of the lower jaw plate 33. This wrapping increases the surface area of the electrode engaging the enlarged tip, improving the mechanical connection while distributing the forces involved. Likewise, the electrical connection between the electrode tab and the contact is enhanced by this arrangement, with the lower conductive surface of the tab engaging the convex, conical surface of the contact tip. Of course, good electrical contact is also made between the angled edge 7c and the contact shoulder 32c. The electrical connector does not pierce the fragile, flexible electrode, yet the force is sufficient to grip the electrode while maintaining excellent electrical contact.

We claim:

1. An electrical connector for connecting to a thin flexible electrode of the type used for medical monitoring, said connector comprising:
   an upper jaw member formed of an insulative material, said upper jaw member having a forward end, a rearward end, first means for pivotally mounting said upper jaw, an angled edge member extending downward from said upper jaw, located forward of said first means for pivotally mounting, and first and second ramp members, extending downward from said upper jaw, on either side of said angled edge member, and tapering toward the forward end of said upper jaw;
   a lower jaw, having a forward end, a rearward end and a second means for pivotally mounting said lower jaw, said second means for pivotally mounting engaging said first means for pivotally mounting such that said forward ends of said upper and lower jaw members may be pivoted into contact with one another;
   spring means for urging said forward ends of said upper and lower jaws together; and
   electrical contact means, mounted to and extending upward from said lower jaw member and including a rearward facing shoulder, said electrical contact means located on said lower jaw such that when said forward ends of said upper and lower jaws are in contact, said electrical contact means is located intermediate said first and second ramps of said upper jaw and such that said rearward facing shoulder of said contact member is located forward of and adjacent to said angled edge member mounted to said upper jaw.

2. An electrical connector according to claim 1 wherein said ramp members on said upper jaw contact said lower jaw along the length of said ramp members when said forward ends of said upper and lower jaws are in contact with one another.

3. An electrical connector for connecting to a thin flexible electrode of the type used for medical monitoring, said connector comprising:
   an upper jaw formed of an insulative material, said upper jaw having a forward end, a rearward end, first means for pivotally mounting said upper jaw intermediate said forward end and said rearward end, and an angled edge member forming a forward facing contact shoulder, extending downward from said upper jaw and located forward of said first means for pivotally mounting;
   a lower jaw having a forward end, a rearward end, and a second means for pivotally mounting said lower jaw intermediate said forward and rearward ends of said lower jaw, said second means for pivotally mounting engaging said first means for pivotally mounting such that said forward ends of said upper and lower jaw members may be pivoted into contact with one another;
   spring means for urging said forward ends of said upper and lower jaws together; and
   electrical contact means, mounted to and extending upward from said lower jaw member, said electrical contact means including a frusto-conical portion extending upward from said lower jaw, said frusto-conical portion tapering toward the forward end of said lower jaw, said frusto-conical surface terminating rearwardly in a rounded contact shoulder located such that when said forward ends of said upper and lower jaws are in contact, said rounded contact shoulder of said contact member is located forward of and adjacent to said angled edge member mounted to said upper jaw.

4. An electrical connector for connecting a thin, flexible, disposable electrode to the lead wire from an electrocardiograph machine comprising:
   a pair of pivotally mounted jaws made of lightweight, electrically insulating material, each of said jaws having a forward end and a rearward end, said jaws mounted pivotally to one another intermediate said forward ends and said rearward ends, one of said jaws having a recess forward of the point where said jaws are pivotally mounted to one another;
   spring means urging said rearward ends of said jaws apart and urging said forward ends of said jaws into contact with each other;
   an electrical contact including an enlarged tip portion positioned in said recess in said one of said jaws with a frusto-conical surface extending towards the other of said jaws, said frusto-conical surface tapering towards said forward end of said one of said jaws the rear of said enlarged tip portion forming a contact shoulder;
   an angled edge member on said other of said jaws extending toward said enlarged tip portion, said angled edge member being located to overlap with, but not engage said contact shoulder so that a tab on said flexible electrode to be received between said jaws is crimped between said angled edge member and said contact shoulder; and depending ramps on said other of said jaws that extend toward said one of said jaws containing said electrical contact, said ramps located to straddle said enlarged tip portion when said forward ends of said jaws are urged into contact with one another to wrap said flexible electrode around said frusto-conical surface of said enlarged tip portion, said ramps being tapered forwardly and extending toward said one of said jaws sufficiently far such that said ramps guide said jaws onto said flexible electrode and prevent said electrode from catching on said angled edge member.

5. An electrical connector for connection to a thin, flexible electrode used in performing electrocardiogram tests comprising:

a pair of pivotally mounted jaws having tips which are biased into gripping position; and an electrical contact supported in one of said jaws having an angled shoulder extending towards the other jaw, an elongated cylindrical portion for connection to an electrical conductor and a tip portion having a convex surface extending towards the other jaw and sloping toward the forward tip of said one jaw; and an angled edge portion carried by said other jaw and extending towards said one jaw closely overlapping but not engaging said shoulder so that the thin flexible electrode placed between the jaws is crimped between the shoulder and the edge portion with a conductive surface of the electrode engaging said contact.

6. An electrical connector for connection to a thin, flexible electrode used in performing electrocardiogram tests comprising:

a pair of pivotally mounted jaws having tips which are biased into gripping position;

an electrical contact supported in one of said jaws having an angled shoulder extending towards the other jaw; and an angled edge portion carried by said other jaw and extending towards said one jaw closely overlapping but not engaging said shoulder so that the thin, flexible electrode placed between the jaws is crimped between the shoulder and the edge portion with a conductive surface of the electrode engaging said contact, the connector further comprising a pair of ramps formed on said other jaw extending downwardly toward said one jaw and sloping toward the forward tip of said other jaw, the ramps being located along the edges of said other jaw and extending towards said one jaw further than said angled edge carried by said other jaw so as to prevent interference between the flexible electrode and said angled edge when positioning the connector jaws on the electrode.

* * * * *

UNITED STATES PATENT AND TRADEMARK OFFICE
CERTIFICATE OF CORRECTION

PATENT NO. : 4,702,256

DATED : October 27, 1987

INVENTOR(S) : Robinson et al.

It is certified that error appears in the above-identified patent and that said Letters Patent are hereby corrected as shown below:

Column 1,
    Line 68, "cam" should be --the--;

Column 4,
    Line 16, after "shoulder" insert --32c (best seen in FIG. 5)--;

Signed and Sealed this

Tenth Day of January, 1989

Attest:

DONALD J. QUIGG

Attesting Officer     Commissioner of Patents and Trademarks